US009771564B2

(12) United States Patent
Muster et al.

(10) Patent No.: US 9,771,564 B2
(45) Date of Patent: Sep. 26, 2017

(54) INFLUENZA VIRUS

(75) Inventors: Thomas Muster, Vienna (AT); Ekaterina Romanovskaya-Romanko, St. Petersburg (RU); Oleg Kiselev, St. Petersburg (RU); Markus Wolschek, Vienna (AT); Boris Ferko, Vienna (AT); Andrej Egorov, Vienna (AT)

(73) Assignee: NANOTHERAPEUTICS, INC., Alachua, FL (US)

(*) Notice: Subject to any disclaimer, the term of this patent is extended or adjusted under 35 U.S.C. 154(b) by 0 days.

(21) Appl. No.: 13/386,355

(22) PCT Filed: Jul. 20, 2010

(86) PCT No.: PCT/EP2010/060489
§ 371 (c)(1),
(2), (4) Date: Feb. 28, 2012

(87) PCT Pub. No.: WO2011/009864
PCT Pub. Date: Jan. 27, 2011

(65) Prior Publication Data

US 2012/0164175 A1 Jun. 28, 2012

Related U.S. Application Data

(60) Provisional application No. 61/227,638, filed on Jul. 22, 2009.

(30) Foreign Application Priority Data

Nov. 5, 2009 (EP) .................................... 09175096

(51) Int. Cl.
*C12N 7/00* (2006.01)
*A61K 39/12* (2006.01)
*C07K 14/005* (2006.01)
*A61K 39/00* (2006.01)

(52) U.S. Cl.
CPC ................ *C12N 7/00* (2013.01); *A61K 39/12* (2013.01); *C07K 14/005* (2013.01); *A61K 2039/5258* (2013.01); *A61K 2039/543* (2013.01); *C12N 2760/16121* (2013.01); *C12N 2760/16122* (2013.01); *C12N 2760/16134* (2013.01); *C12N 2760/16161* (2013.01)

(58) Field of Classification Search
CPC ........... C12N 2760/16134; C12N 2760/16234; C12N 2760/16261; C12N 2760/16111; C12N 2740/15034; C12N 2760/16022; C12N 2770/20022; C12N 2710/16634
See application file for complete search history.

(56) References Cited

U.S. PATENT DOCUMENTS

2009/0074804 A1 3/2009 Lee et al.
2010/0136052 A1* 6/2010 Wolschek et al. ......... 424/206.1
2011/0262481 A1* 10/2011 Muster et al. ............ 424/206.1

FOREIGN PATENT DOCUMENTS

WO WO/99/64068 12/1999
WO WO/99/64571 12/1999
WO WO/2008/043805 4/2008

OTHER PUBLICATIONS

Zamarin D, Ortigoza MB, Palese P. Influenza A virus PB1-F2 protein contributes to viral pathogenesis in mice. J Virol. Aug. 2006;80(16):7976-83.*

Jackson D, Hossain MJ, Hickman D, Perez DR, Lamb RA. A new influenza virus virulence determinant: the NS1 protein four C-terminal residues modulate pathogenicity. Proc Natl Acad Sci U S A. Mar. 18, 2008;105(11):4381-6. Epub Mar. 11, 2008.*

Ozawa M, Basnet S, Burley LM, Neumann G, Hatta M, Kawaoka Y. Impact of amino acid mutations in PB2, PB1-F2, and NS1 on the replication and pathogenicity of pandemic (H1N1) 2009 influenza viruses. J Virol. May 2011;85(9):4596-601. Epub Feb. 16, 2011.*

Krenn BM, et. al. Single HA2 mutation increases the infectivity and immunogenicity of a live attenuated H5N1 intranasal influenza vaccine candidate lacking NS1. PLoS One. Apr. 7, 2011;6(4):e18577.*

Chew T, Noyce R, Collins SE, Hancock MH, Mossman KL. Characterization of the interferon regulatory factor 3-mediated antiviral response in a cell line deficient for IFN production. Mol Immunol. Jan. 2009;46(3):393-9. Epub Nov. 26, 2008.*

Haye K, Burmakina S, Moran T, Garcia-Sastre A, Fernandez-Sesma A. The NS1 protein of a human influenza virus inhibits type I interferon production and the induction of antiviral responses in primary human dendritic and respiratory epithelial cells. J Virol. Jul. 2009;83(13):6849-62. doi: 10.1128/JVI.02323-08. Epub Apr. 29, 2009.*

Soubies SM, Hoffmann TW, Croville G, Larcher T, Ledevin M, Soubieux D, Quéré P, Guérin JL, Marc D, Volmer R. Deletion of the C-terminal ESEV domain of NS1 does not affect the replication of a low-pathogenic avian influenza virus H7N1 in ducks and chickens. J Gen Virol. Jan. 2013;94(Pt 1):50-8. Epub Oct. 10, 2012.*

Wressnigg N, Voss D, Wolff T, Romanova J, Ruthsatz T, Mayerhofer I, Reiter M, Nakowitsch S, Humer J, Morokutti A, Muster T, Egorov A, Kittel C. Development of a live-attenuated influenza B DeltaNS1 intranasal vaccine candidate. Vaccine. May 11, 2009;27(21):2851-7. Epub Mar. 11, 2009.*

Garcia-Sastre A, Egorov A, Matassov D, Brandt S, Levy DE, Durbin JE, Palese P, Muster T. Influenza A virus lacking the NS1 gene replicates in interferon-deficient systems. Virology. Dec. 20, 1998;252(2):324-30.*

Conenello GM, Palese P. Influenza A virus PB1-F2: a small protein with a big punch. Cell Host Microbe. Oct. 11, 2007;2(4):207-9.*

(Continued)

*Primary Examiner* — Rachel B Gill
(74) *Attorney, Agent, or Firm* — John M. Garvey; DLA Piper LLP (US)

(57) ABSTRACT

The present invention provides a novel influenza virus wherein both the NS and the PB1 gene segments are modified and wherein the PB1-F2 open reading frame is modified by introduction of at least one stop codon. Specifically, the influenza virus is lacking functional NS1 and PB1-F2 proteins. Additionally, a vaccine formulation comprising the modified influenza virus is provided and its use for prevention of influenza vaccination.

10 Claims, 8 Drawing Sheets

(56) References Cited

OTHER PUBLICATIONS

Figure 1:
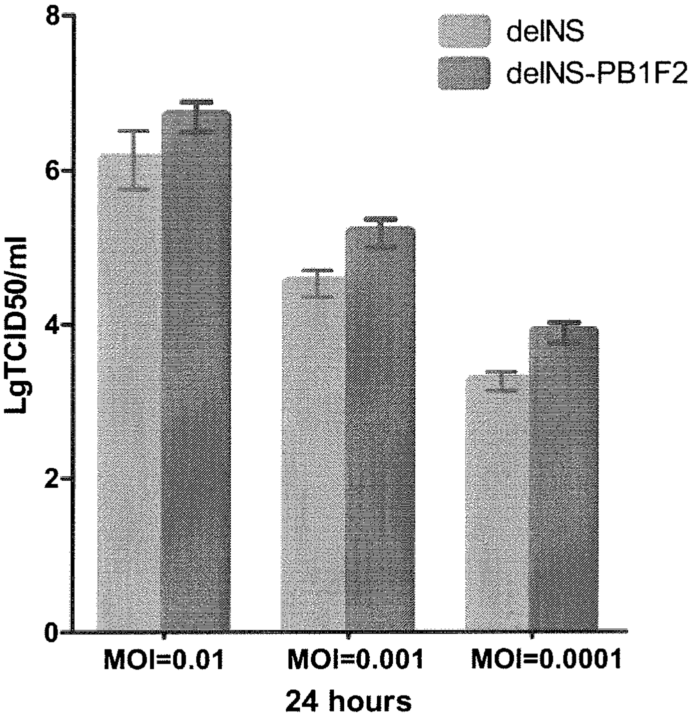

Extended European Search Report, European Patent Application No. 09175096.8-1223, Mar. 22, 2010.
International Preliminary Report on Patentability, International Patent Application No. PCT/EP2010/060489, Jan. 24, 2012.
International Search Report and Written Opinioin, Patent Application No. PCT/EP2010/060489, Sep. 16, 2010.
B. Ferko et al., Journal of Virology, 78(23):13037-13045 (2004).
Chen et al., Nature Medicine, 7(12)1306-1312 (2001).
Chien et al., Biochemistry, 43(7):1950-1962 (2004).
Enami and Enami, J. Virol, 74(12):5556-5561 (2000).
Herlocher, M. L., A. C. Clavo, and H. F. Maassab, Virus Res., 42:11-25 (1996).
Herlocher, M. L., H. F. et al., Proc Natl Acad Sci USA, 90:6032-6036 (1993).
Hoffmann et al., PNAS, 97(11):6108-6113 (2000).
Jackson D. et al., PNAS, 105:4381-4386 (2008).
Lamb RA & Krug RM, "Orthomyxoviridae: the viruses and their replication," pp. 1353-1395 (1996).
Min J. et al., Proc.Natl.Acad.Sci, 103:7100-7105 (2006).
Neumann and Kawaoka, Adv. Virus Res., 53:265-300 (1999).
Pleschka S. et al., J. Virol., 70(6):4188-4192 (1996).
Romanova J et al., PLoS ONE, 4( e5984):1-12 (2009).
Schultz-Cherry S. et al., J. Virol., 75(17):7875-7881 (2001).
Treanor, J., M. et al., J Virol., 68:7684-7688 (1994).
Yoneyama M. et al., Nat. Immunol., 5:730-737 (2004).
Zamarin D. et al., J. Virol., 80(16):7976-7983 (2006).
Zell et al J., Gen. Virology, 88:536-546 (2007).
Kochs et al., 2007, "Properties of H7N7 influenza A virus strain SC35M lacking interferon antagonist NS1 in mice and chickens," Journal of General Virology 88:1403-1409.
McAuley, Julie L. et al., Expression of the 1918 Influenza A Virus PB1-F2 Enhances the Pathogenesis of Viral and Secondary Bacterial Pneumonia, Cell Host & Microbe 2, 240-249, Oct. 2007, Elsevier Inc.

* cited by examiner

Fig. 3

SEQID1: GHB01 PB1

AGCGAAAGCAGGCAAACCATTTGAATGGATGTCAATCCGACTTTACTTTTC
TTGAAAATTCCAGCGCAAAATGCCATAAGCACCACATTCCCTTATACTGGAGATC
CTCCATACAGCCATGGAACAGGAACAGGATACACCATGGACACAGTTAACAGAA
CACATCAATATTCAGAAAAAGGGAAATGGACAACAAACACAGAAACTGGGGCGC
CCCAACTTAACCCGATTGATGGACCACTACCTGAGGATAATGAGCCAAGTGGATA
TGCACAAACAGACTGTGTCCTGGAAGCTATGGCTTTCCTTGAGGAATCCCACCCA
GGGATCTTTGAAAACTCGTGCCTTGAAACAATGGAAGTCGTTCAACAAACAAGAG
TGGACAGACTGACCCAAGGTCGTCAGACCTATGATTGGACATTAAACAGAAATCA
ACCAGCCGCAACTGCATTAGCCAACACTATAGAAGTTTTCAGATCGAATGGTCTA
ACAGCTAATGAGTCGGGAAGGCTAATAGATTTCCTCAAGGATGTGATGGAATCAA
TGGATAAAGAGGAAATAGAGATAACAACACACTTCCAAAGAAAAAGAAGAGTAAG
AGACAACATGACCAAGAAAATGGTCACACAAAGAACAATAGGAAAGAAAAAGCAG
AGAGTGAACAAGAGAAGCTATCTAATAAGAGCATTAACTTTGAACACAATGACCA
AAGATGCAGAAAGAGGTAAATTAAAGAGAAGAGCTATTGCAACACCCGGGATGC
AAATCAGAGGGTTCGTGTACTTTGTTGAAACTCTAGCTAGGAGCATTTGTGAGAA
GCTTGAACAGTCTGGACTTCCAGTAGGAGGTAATGAAAAGAAGGCCAAACTGGC
AAATGTTGTGAGAAAGATGATGACTAATTCACAAGACACAGAGCTTTCTTTCACAA
TTACTGGAGACAATACTAAGTGGAATGAAAATCAAAATCCTCGAATGTTCCTGGC
GATGATTACATATATCACAAAAAATCAACCTGAATGGTTCAGAAACATCCTGAGCA
TCGCACCCATAATGTTCTCAAACAAAATGGCGAGACTAGGGAAAGGATACATGTT
CGAAAGTAAGAGAATGAAGCTCCGAACACAAATACCAGCAGAAATGCTAGCAAG
CATTGACCTAAAGTATTTCAATGAATCAACAAGAAAGAAAATTGAGAAAATAAGGC
CTCTTCTAATAGATGGCACAGCGTCATTGAGCCCTGGAATGATGATGGGCATGTT
CAACATGCTAAGTACGGTTTTAGGAGTCTCAATACTGAATCTTGGGCAAAAGAAA
TACACCAAAACAACATACTGGTGGGATGGGCTTCAATCCTCTGATGATTTTGCTC
TCATAGTGAATGCACCAAATCATGAGGGAATACAAGCAGGAGTGGATAGATTCTA
CAGAACCTGCAAGCTAGTCGGAATCAATATGAGCAAGAAGAAGTCCTATATAAAT
AGGACAGGAACATTTGAATTCACAAGCTTTTTTTATCGCTATGGATTTGTGGCCAA
TTTTAGCATGGAGCTGCCCAGTTTTGGAGTGTCTGGGATTAATGAATCAGCTGAT
ATGAGCATTGGAGTAACAGTGATAAAGAACAACATGATAAACAATGACCTTGGAC

Fig. 3 Cont.

CAGCAACAGCCCAGATGGCTCTTCAACTGTTCATCAAGGACTACAGATATACATA
TCGGTGCCACAGAGGAGACACACAAATTCAGACGAGGAGATCATTTGAGCTAAA
GAAGCTGTGGGAGCAAACCCGATCAAAGGCAGGACTATTGGTTTCAGATGGAGG
ACCGAACTTATACAATATCCGGAATCTTCACATCCCTGAAGTCTGCTTAAAGTGG
GAGCTAATGGATGAAGACTATCAGGGAAGACTTTGTAATCCCCTGAATCCATTTG
TCAGCCATAAAGAGATTGAGTCTGTAAACAATGCTGTGGTAATGCCAGCTCATGG
TCCAGCCAAGAGCATGGAATATGACGCTGTTGCAACTACACACTCCTGGATTCCC
AAGAGGAACCGCTCTATTCTCAACACAAGCCAAAGGGGAATTCTTGAGGATGAAC
AGATGTATCAGAAGTGCTGCAACCTGTTCGAGAAATTTTTCCCCAGTAGTTCATA
CAGGAGACCGGTTGGAATTTCCAGCATGGTGGAGGCCATGGTGTCTAGGGCCC
GGATTGATGCCAGAATTGACTTCGAGTCTGGACGGATTAAGAAAGAAGAGTTCTC
CGAGATCATGAAGATCTGTTCCACCATTGAAGAGCTCAGACGGCAAAAACAATGA
ATTTAGCTTGTCCTTCATGAAAAAATGCCTTGTTTCTACT

Fig. 4

SEQID2: GHB01 PB1delF2

AGCGAAAGCAGGCAAACCATTTGAATGGATGTCAATCCGACTTTACTTTTC
TTGAAAATTCCAGCGCAAAATGCCATAAGCACCACATTCCCTTATACTGGAGATC
CTCCATACAGCCACGGAACAGGAACAGGATACACCATGGACACAGTGAACAGAA
CACATCAATATTCAGAAAAAGGGAAATGGACAACAAACACAGAAACTGGGGCGC
CCCAACTAAACCCGATTGACGGACCACTACCTGAGGATAACGAGCCAAGTGGAT
ACGCACAAACAGACTGTGTCCTAGAAGCTATGGCTTTCCTTGAGGAATCCCACCC
AGGGATCTTTGAAAACTCGTGCCTTGAAACAATGGAAGTCGTTCAACAAACAAGA
GTGGACAGACTGACCCAAGGTCGTCAGACCTATGATTGGACATTAAACAGAAATC
AACCAGCCGCAACTGCATTAGCCAACACTATAGAAGTTTTCAGATCGAATGGTCT
AACAGCTAATGAGTCGGGAAGGCTAATAGATTTCCTCAAGGATGTGATGGAATCA
ATGGATAAAGAGGAAATAGAGATAACAACACACTTCCAAAGAAAAAGAAGAGTAA
GAGACAACATGACCAAGAAAATGGTCACACAAAGAACAATAGGAAAGAAAAAGCA
GAGAGTGAACAAGAGAAGCTATCTAATAAGAGCATTAACTTTGAACACAATGACC
AAAGATGCAGAAAGAGGTAAATTAAAGAGAAGAGCTATTGCAACACCCGGGATG
CAAATCAGAGGGTTCGTGTACTTTGTTGAAACTCTAGCTAGGAGCATTTGTGAGA
AGCTTGAACAGTCTGGACTTCCAGTAGGAGGTAATGAAAAGAAGGCCAAACTGG
CAAATGTTGTGAGAAAGATGATGACTAATTCACAAGACACAGAGCTTTCTTTCACA
ATTACTGGAGACAATACTAAGTGGAATGAAAATCAAAATCCTCGAATGTTCCTGG
CGATGATTACATATATCACAAAAAATCAACCTGAATGGTTCAGAAACATCCTGAGC
ATCGCACCCATAATGTTCTCAAACAAAATGGCGAGACTAGGGAAAGGATACATGT
TCGAAAGTAAGAGAATGAAGCTCCGAACACAAATACCAGCAGAAATGCTAGCAAG
CATTGACCTAAAGTATTTCAATGAATCAACAAGAAAGAAAATTGAGAAAATAAGGC
CTCTTCTAATAGATGGCACAGCGTCATTGAGCCCTGGAATGATGATGGGCATGTT
CAACATGCTAAGTACGGTTTTAGGAGTCTCAATACTGAATCTTGGGCAAAAGAAA
TACACCAAAACAACATACTGGTGGGATGGGCTTCAATCCTCTGATGATTTTGCTC
TCATAGTGAATGCACCAAATCATGAGGGAATACAAGCAGGAGTGGATAGATTCTA
CAGAACCTGCAAGCTAGTCGGAATCAATATGAGCAAGAAGAAGTCCTATATAAAT
AGGACAGGAACATTTGAATTCACAAGCTTTTTTTATCGCTATGGATTTGTGGCCAA
TTTTAGCATGGAGCTGCCCAGTTTTGGAGTGTCTGGGATTAATGAATCAGCTGAT
ATGAGCATTGGAGTAACAGTGATAAAGAACAACATGATAAACAATGACCTTGGAC
CAGCAACAGCCCAGATGGCTCTTCAACTGTTCATCAAGGACTACAGATATACATA

Fig. 4 Cont.

TCGGTGCCACAGAGGAGACACACAAATTCAGACGAGGAGATCATTTGAGCTAAA
GAAGCTGTGGGAGCAAACCCGATCAAAGGCAGGACTATTGGTTTCAGATGGAGG
ACCGAACTTATACAATATCCGGAATCTTCACATCCCTGAAGTCTGCTTAAAGTGG
GAGCTAATGGATGAAGACTATCAGGGAAGACTTTGTAATCCCCTGAATCCATTTG
TCAGCCATAAAGAGATTGAGTCTGTAAACAATGCTGTGGTAATGCCAGCTCATGG
TCCAGCCAAGAGCATGGAATATGACGCTGTTGCAACTACACACTCCTGGATTCCC
AAGAGGAACCGCTCTATTCTCAACACAAGCCAAAGGGGAATTCTTGAGGATGAAC
AGATGTATCAGAAGTGCTGCAACCTGTTCGAGAAATTTTTCCCCAGTAGTTCATA
CAGGAGACCGGTTGGAATTTCCAGCATGGTGGAGGCCATGGTGTCTAGGGCCC
GGATTGATGCCAGAATTGACTTCGAGTCTGGACGGATTAAGAAAGAAGAGTTCTC
CGAGATCATGAAGATCTGTTCCACCATTGAAGAGCTCAGACGGCAAAAACAATGA
ATTTAGCTTGTCCTTCATGAAAAAATGCCTTGTTTCTACT

Fig. 5

SEQID 3: GHB01 PB1F2

MEQEQDTPWTQLTEHINIQKKGNGQQTQKLGRPNLTRLMDHYLRIMSQVDM HKQTVSWKLWLSLRNPTQGSLKTRALKQWKSFNKQEWTD&

Fig. 6

SEQID 4: GHB01 delF2

TEQEQDTPWTQ&TEHINIQKKGNGQQTQKLGRPN#TRLTDHYLRITSQVDTH KQTVS@KLWLSLRNPTQGSLKTRALKQWKSFNKQEWTD&

&…TGA

#...TAA

@…TAG

INFLUENZA VIRUS

CROSS-REFERENCE TO RELATED APPLICATIONS

This application is the U.S. national stage of International Patent Application No. PCT/EP2010/060489, filed on Jul. 20, 2010 and entitled NOVEL INFLUENZA VIRUS, which claims the benefit of priority from U.S. Patent Application No. 61/227,638, filed Jul. 22, 2009, and from European Patent Application No. 09175096.8, filed Nov. 5, 2009. The disclosures of the foregoing applications are incorporated herein by reference in their entirety.

SEQUENCE LISTING

The instant application contains a Sequence Listing which has been filed electronically in ASCII format and is hereby incorporated by referenced in its entirety. Said ASCII copy, created on Jun. 20, 2017, is named BAX-679_SL.txt and is 9,585 byes in size.

BACKGROUND

The present invention provides a novel influenza virus wherein both the NS and the PB1 gene segments are modified and wherein the PB1-F2 ORF is modified by introduction of at least one stop codon. According to a specific embodiment, the influenza virus is lacking functional NS1 and PB1-F2 proteins and is replication deficient in interferon competent cells.

Additionally, a vaccine formulation comprising said modified influenza virus is provided and its use for prevention of influenza infection.

BACKGROUND OF THE INVENTION

Influenza A virus is one of the most common pathogens threatening humans and animals, with the potential to cause disastrous pandemics. Influenza A virus causes 300,000-500,000 deaths worldwide each year, and in pandemic years, this number can increase to 1 million (in 1957-1958) or can be as high as 50 million, as was seen in 1918-1919. More recently, highly pathogenic avian influenza viruses (H5N1) have generated great concern regarding their potential to cause a pandemic. H5N1 infections in humans were seen in Hong Kong in a small outbreak in 1997 that resulted in 18 human infections and six fatalities, and reached up to now 383 human cases with a 61% fatality rate.

Inactivated influenza vaccines which are licensed in Europe have limited protection efficacy especially in elderly population and in small children who never experienced natural influenza. Cold-adapted live influenza vaccines are more effective in children preventing and curbing the spread of disease, but new technologies such as reverse genetics can now be used for further improvement of the live vaccine approach.

The concept of the current live attenuated vaccine is based on the generation of a temperature sensitive attenuated "master strain" adapted to grow at 25° C. (cold adaptation). Live cold adapted and inactivated virus vaccine stimulate the immune system differently, yet in both cases lack of sufficient immunogenicity especially in elderly persons is one of the most important drawbacks in influenza vaccination.

Although ca live influenza virus vaccines are considered as sufficiently safe, the exact genetic and molecular mechanisms of attenuation are not completely understood. It is claimed that the nature of the safety of cold-adapted influenza vaccines is based on a large number of point mutations distributed across the internal gene segments. However, only a small number of mapped mutations localized in the polymerase genes are responsible for the attenuation of cold-adapted virus strains that are unable to replicate at normal body temperature (Herlocher, M. L., A. C. Clavo, and H. F. Maassab. 1996, Virus Res. 42:11-25; Herlocher, M. L., H. F. et al., 1993, Proc Natl Acad Sci USA. 90:6032-6036). In fact, the genetic stability of live vaccine strains are often questioned since viruses re-isolated from vaccinated hosts reveal additional point mutations which might eventually function as "suppressor" mutations causing enhanced replication properties and a possible loss of the temperature sensitive phenotype of the revertant virus (Herlocher, M. L., H. F. et al., 1993, Proc. Natl. Acad. Sci. 90:6032-6036, Treanor, J., M. et al., 1994 J Virol. 68:7684-7688.).

The new knowledge in influenza genetics provides guidance for construction of ideal vaccine strains for live vaccine where all major pathogenicity factors might be eradicated by targeted genetic engineering. Influenza A virus contains segmented, negative-stranded RNA genome (Lamb & Krug, 1996). Eight segments encode the subunits of the transcriptase complex (PB1, PB2, PA, nucleoprotein NP), three integral membrane proteins (haemagglutinin HA, neuraminidase NA, proton channel M2), the matrix protein (M1), the nuclear export protein (NS2/NEP) and nonstructural multifunctional pathogenicity factor NS1.

It was demonstrated that deletion of the NS1 protein leads to a significant attenuation of influenza virus due to lack of replication in interferon competent cells or organisms (replication deficient phenotype). Viruses lacking the NS1 protein are not able to antagonize cytokine production of infected cells, therefore inducing self-adjuvanting and immune modulating effects. The hallmark of immune response after immunization with DelNS1 virus is triggering of Th1 type of immune response associated with predominant IgG2A antibody isotype response (B. Ferko et al. 2002).

The existence of an eleventh protein encoded by an alternative ORF of segment 2 was reported (Chen et al., 2001). This pro-apoptotic protein interacting with the mitochondrial proteins ANT3 (adenine nucleotide translocator 3) and VDAC1 (voltage dependent anion channel 1) is considered as an important pathogenicity factor. Cell-type dependent induction of cell death induced by PB1-F2 was observed in infected host immune cells, but not in epithelial cells. It is likely that the enhancement of viral pathogenicity is due to apoptosis of the infected immune cells, which delays the immune response. It is speculated that during the initial stages of viral replication, antigen presentation by professional antigen-presenting cells such as macrophages and dendritic cells may be impaired by PB1-F2 function.

Deletion of PB1-F2 ORF from several influenza strains caused an effect of partial attenuation of the virus due to accelerated clearance of the virus from respiratory tract of mice (Zamarin D. et al., J. Virol. 2006, 7976-7983). Nothing is known about possible involvement of PB1-F2 protein in regulation of innate or adaptive immune response or in growth properties of the virus.

Romanova et al. describes the preclinical evaluation of a replication deficient, live attenuated delNS1 H5N1 influenza vaccine candidate. The vaccine formulation is studied in three animal models and is administered to mice, ferrets and macaques. The vaccine did not show shedding in the vaccinated animals after intranasal administration (PLOS ONE, Vol 4, Article E5984).

Zell et al. describes a comprehensive evaluation of the Influenza A PB1-F2 sequences to gain a detailed view on the prevalence of PB1-F2. (J. Gen. Virology, 2007, 88, pp. 536-546).

WO2008/043805 describes amphotericin B as supplement for influenza virus cultivation.

US2009/0074804 discloses isolated influenza strains suitable for vaccine production for mammals containing at least one modified influenza protein.

In view of the current need on safe and efficient vaccine supply it is an object of the invention to improve current vaccine strains in terms of their safety and immunogenicity and to develop a new generation of intranasal influenza vaccine suitable for prophylaxis of seasonal and pandemic influenza in people, especially in small children younger than 3 years old—the age group where conventional inactivated parenteral vaccines may be not effective.

The object is achieved by the provision of the embodiments of the present application.

DESCRIPTION OF THE INVENTION

It has been surprisingly found that the immunogenic potential of DelNS1 reassortant virus comprising lack of functional NS1 protein or having partial deletions of the NS1 protein in mice can be boosted by additional modification or deletion of PB1-F2. Deletion of PB1-F2 can promote IgG1 (Th2 type) and IgG2a (Th1 type) immune response. Such effect shows that double modification or deletion can be desirable for construction of more efficient vaccine strains for intranasal vaccination.

Alternatively, it has also been surprisingly found that influenza virus comprising modified NS and PB1 gene segments have shown increased growth in cell culture within the first 24 hours after infection. Thus double mutants, specifically those lacking functional NS1 and PB1-F2 proteins appear to be capable of more efficient replication when compared to influenza virus strains with a deletion of the NS1 protein only.

The present invention therefore provides an influenza virus wherein the NS and the PB1 gene segments are modified and (and wherein the PB1-ORF (open reading frame) is modified by introduction of at least one stop codon or elimination of at least one methionine/start codon without alteration of the PB1 amino acid sequence.

Preferably, the influenza virus is a replication deficient virus.

According to a specific embodiment, the replication deficient influenza virus comprises a PB1 segment which is modified by introduction of multiple stop codons and/or elimination of methionine codons within the PB1-F2 ORF. More specifically the modifications are at any of nucleotide positions T120, T153, T222, T234, T255, T270 and G291 according to the numbering of SEQ ID No. 1.

Even more specifically the modification of the PB1 gene results in the knock out of the PB1-F2 open reading frame (ORF).

According to an embodiment of the invention the influenza virus comprises the nucleotide sequence of SEQ ID. No 2 or at least part thereof.

Specifically, the PB1F2 protein comprises the amino acid sequence of SEQ ID No. 4 or part thereof.

According to the invention the NS gene segment of the virus comprises a modification, substitution and/or deletion of at least one nucleotide, specifically encoding a truncated NS1 protein, even more specifically entirely lacking the NS1 protein.

The influenza virus can specifically lack functional NS1 and/or functional PB1-F2 proteins.

According to a further embodiment, a vaccine formulation comprising the virus of the invention and optionally a pharmaceutically acceptable carrier is provided, said vaccine being specifically formulated for intranasal delivery. Furthermore, the invention provides a method for preventing influenza virus infection of a patient comprising administering the inventive vaccine to an individual.

The invention also provides the use of the inventive virus for preparing a preparation for preventing influenza virus infection of an individual.

FIGURES

FIG. 1: Vero cell were infected with delNS1 (delNS) and delNS1-PB1-delF2 (delNS1-PB1-delF2) virus variants as described in Material and Methods section in more detail. Irrespective of the MOI used, the delNS1-PB1-delF2 virus variant replicated to significantly higher TCID50 titers 24 hours post infection when compared with delNS virus. The data indicate that deletion of the F2 protein has a positive effect on virus growth in the production substrate—the Vero cells.

Figure 2:
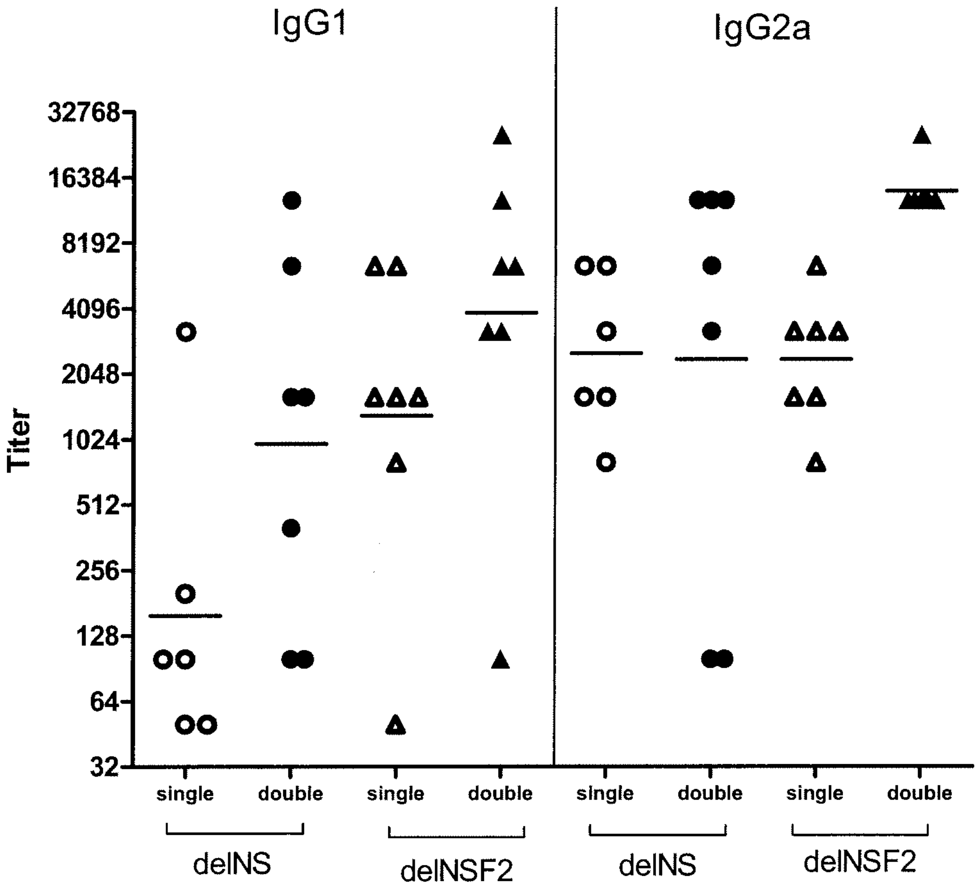

FIG. 2: Mice were immunized twice with delNS1-PB1-delF2 (delNSF2) and delNS1 (delNS) virus mutants. Serum samples collected at day 28 after first immunization (single) and at day 20 after second immunization (double) were analyzed for the presence of virus-specific IgG1 and IgG2a antibodies. Shown are end-point titres of individual mice. Horizontal line segments represent the geometric mean titer of the entire group of mice immunized with the respective virus variant as indicated in the figure.

FIG. 3: SEQID1: nucleotide sequence of GHB01 PB1 gene

FIG. 4: SEQID2: nucleotide sequence of GHB01 PB1delF2

FIG. 5: SEQID 3: amino acid sequence of GHB01 PB1F2 protein

FIG. 6: SEQID 4: amino acid sequence of GHB01 PB1delF2 showing introduced stop codons and eliminated methionine/start codons. Amino acid substitutions compared to GHB01 PB1F2 are highlighted in bold, underlined letters.

Figure 7:
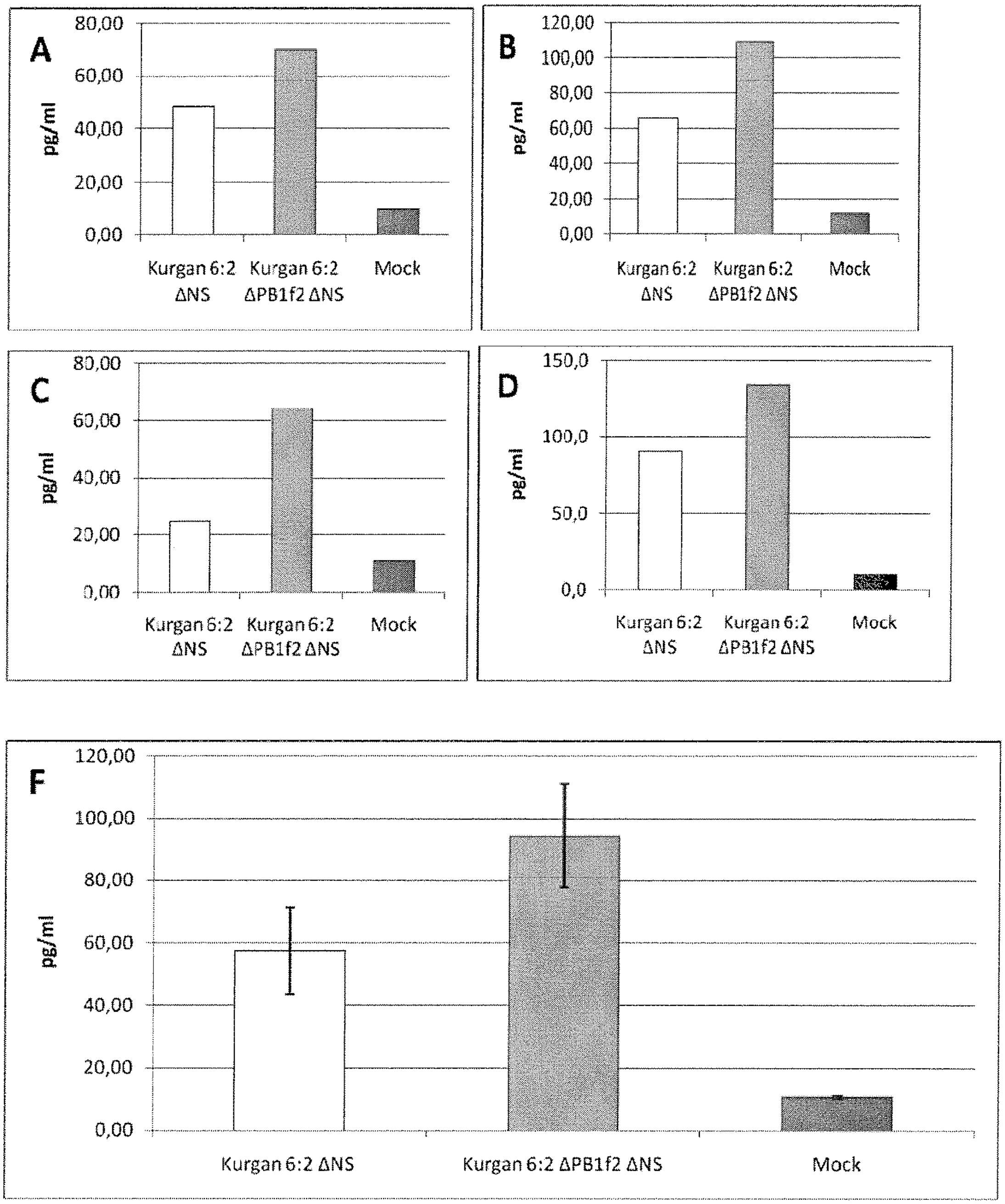

FIG. 7: Induction of IFN-α in Human PBMCs, IFN-α levels (pg/ml) 6 h p.i. A, B, C and D show individual donor data; F is the summarizing graphic (data are presented as a mean of four volunteers data±SEM).

DETAILED DESCRIPTION OF THE INVENTION

The present invention provides an influenza virus wherein both the NS and the PB1 gene segments are modified.

Specifically, the influenza virus of the invention is a replication deficient virus.

According to a specific embodiment of the invention the PB1 gene is modified by introduction of at least one stop codon into the ORF coding for the PB1-F2 protein.

The term "gene" or "gene segment" or "segment" is defined in the application as consisting of the complete sequence according to the listed SEQ. Ids. or comprising at least part or fragment thereof.

The inventive influenza virus can be Influenza A, B or C virus. Preferably it is influenza A virus. Exemplarily, it can be H5N1, H3N2, H1N1 or any reassortant derived therefrom.

It is believed that by means of depletion of immunocytes at the site of virus entry and replication, pathogenic influenza strains can down-regulate the innate immune response and development of specific immunity. Thus, PB1-F2 protein is considered as one of the accessory factors for entry of new pandemic strains into human population. All influenza pandemic strains of the 20$^{th}$ century and the most pathogenic seasonal H2N2, H3N2 influenza A strains encode functionally active PB1-F2 protein, whereas majority of less pathogenic modern H1N1 strains contain truncated versions of this protein. Nothing is known so far about how deletion of PB1-F2 protein can modulate the immune response.

According to specific embodiment of the invention the PB1 segment is modified by introduction of multiple stop codons at any nucleic acid position within the PB1-F2 ORF leading to knock out of the PB1-F2 open reading frame (ORF). Specifically, all codons coding for amino acid methionine are modified. For example, the modifications can be at any of nucleotide positions T120, T153, T222, T234, T255, T270 and G291 according to the nucleotide numbering of SEQ ID1. More specifically, nucleotides at positions 153, 222 and/or 291 are substituted to comprise a stop codon.

According to the invention the term "multiple stop codons" means that at least two, preferably at least three stop codons are introduced into the respective gene.

The term "modification" in connection with the PB1-F2 ORF means that at least one nucleotide is replaced by a different nucleotide resulting in a change of the parental nucleotide sequence. Alternatively, at least one amino acid is replaced resulting in a change of the parental amino acid sequence.

Specifically, the influenza virus has a modification of the PB1 gene which results in the knock out of the complete PB1-F2 ORF. This can be performed by introducing at least one stop codon into the PB1-F2 ORF, preferably at least two stop codons, more preferred at least three stop codons Preferably, introduction of at least one stop codon into the PB1-F2 ORF is performed without altering the amino acid sequence of PB1.

More specifically, the influenza virus of the invention contains a PB1-F2 protein comprising at least one of the stop codons according to SEQ ID. No 4, preferably at least two, more preferred three stop codons according to SEQ ID. No 4. More specific, the PB1-F2 protein has the amino acid sequence of SEQ ID No. 4

The NS1 protein of influenza A virus is a multifunctional protein that consists of approximately 230 amino acids and is early and abundantly synthesized in infection. It counters cellular antiviral activities and is a virulence factor. By the activity of its carboxy terminal region, the NS1 protein is able to inhibit the host mRNA's processing mechanisms. Second, it facilitates the preferential translation of viral mRNA by direct interaction with the cellular translation initiation factor. Third, by binding to dsRNA and interaction with putative cellular kinase(s), the NS1 protein is able to prevent the activation of interferon (IFN-) inducible dsRNA-activated kinase (PKR), 2'5'-oligoadenylate synthetase system and cytokine transcription factors.

Fourth, the N terminal part of NS1 binds to RIG-I and inhibits downstream activation of IRF-3, preventing the transcriptional induction of IFN-β. Therefore the NS1 protein inhibits the expression of IFN-α or IFN-β genes, delays the development of apoptosis in the infected cells, and prevents the formation of the antiviral state in neighbouring cells. Influenza viruses containing modifications within the NS1 protein are known in the art. For example, WO 99/64571 describes the complete knock out of the NS gene segment, WO 99/64068 discloses various NS gene segments that have been partially deleted.

The term "modification" with regard to the NS1 is defined that at least one nucleotide is inserted, deleted or substituted by a different nucleotide resulting in a change of the parental nucleotide sequence. Alternatively, at least one amino acid is inserted, deleted or replaced resulting in a change of the parental amino acid sequence.

The modification of the NS gene can comprise any modification, substitution and/or deletion of at least one nucleotide, specifically the NS gene can encode a truncated NS1 protein or, as a preferred alternative, contains a deletion within the NS1 ORF leading to an influenza virus lacking the functional NS1 protein.

According to the present invention the modification within the NS1 protein can provide a replication deficient influenza virus or an influenza virus that shows reduced replication in interferon competent cells.

In one approach, portions of the amino terminal region of the NS1 gene product are retained whereas portions of the C-terminal region of the NS1 gene product are deleted.

Specifically desired mutations can be engineered by way of nucleic acid insertion, deletion, or mutation at the appropriate codon. In particular, the truncated NS1 proteins still comprise amino acids from 1-60, 1-70 amino acids, 1-80 amino acids, 1-90 amino acids (the N-terminal amino acid is 1), and specifically 90 amino acids; from 1-100 amino acids, and specifically comprise 1-99 amino acids; from 1-110 amino acids; from 1-120 amino acids; or from 1-130 amino acids, and specifically 124 amino acids of the wildtype NS1 gene product. In an alternative embodiment the modified NS1 protein comprises a deletion of at least 50% of the NS1 amino acids, preferably of at least 70%, more preferably of at least 90%. Alternatively, the functionality of the NS1 protein can be completely diminished.

The NS1 protein of the influenza virus vector according to the invention lacks the functional RNA binding domain. The primary function of this domain located at the amino end of the NS1 protein (amino acids 1-73) is binding dsRNA and inhibiting the 2'5'oligo (A) synthetase/RNase L pathway (Min J. et al., Proc. Natl. Acad. Sci, 2006, 103, 7100-7105, Chien et al., Biochemistry. 2004 Feb. 24; 43(7):1950-62) as well as the activation of a cytoplasmic RNA helicase, RIG-I, retinoic acid-inducible protein I (Yoneyama M. et al., Nat. Immunol., 2004, 5, 730-737).

Lack of a functional RNA binding domain is defined according to the present invention as complete lack of dsRNA binding ability leading to an influenza virus that does not replicate in interferon competent cells.

According to an embodiment of the invention the effector domain of the NS1 protein of influenza virus vector is not functional. The effector domain interacts with cellular proteins to inhibit mRNA nuclear export. The effector domain is located at the C-terminal part of the NS1 protein. According to Schultz et al. the effector domain is specifically located between amino acid residues 117 and 161, other literature locates the effector domain between 134 and 161. The NS1 effector domain can be completely or partially deleted as well as amino acids can be substituted or inserted and the remaining effector domain can be tested for functionality as described in the art (Schultz-Cherry S. et al., J. Virol., 2001, 7875-7881).

According to a further embodiment of the invention, the C-terminal amino acids relevant for effector binding activity are modified to inhibit effector function. Specifically at least one amino acid at any one of positions 74 to 230, more specifically at least one amino acid at any one of positions 116 to 161, more specifically at any one of positions 134 to 161 is modified. According to a preferred embodiment, the modification is a deletion of amino acids at positions 74 to 230, specifically at positions 116 to 161, more specifically at positions 134 to 161.

A reverse genetics system on Vero cells for developing reassortants and/or expression of modified recombinant influenza virus strains can be used. The technology is already well known in the art (Pleschka S. et al., 1996, J. Virol., 70(6), 4188-4192, Neumann and Kawaoka, 1999, Adv. Virus Res., 53, 265-300, Hoffmann et al. 2000, Proc Natl Acad Sci USA. 97:6108-13). Alternatively, the technology based on RNPs as described by Enami and Enami (J. Virol, 2000, 74, 12, pp. 5556-5561) can be used for developing reassortants. Alternatively, a reversed genetics system can be used wherein helper virus is present.

More specifically, the virus selected for use in the invention comprises a modified NS gene leading to an influenza virus that is attenuated, i.e. it is infectious and can replicate in vitro in interferon deficient cells or cell systems but does not replicate or shows highly reduced replication activity in interferon competent cells. According to the invention the term "replication deficient" is defined as replication rate in interferon competent host cells that is at least less than 5%, preferably less than 1%, preferably less than 0.1% than wild type influenza virus as determined by hemagglutination assay, TCID50 assay or plaque assay as well known in the art.

According to a specific embodiment of the invention, the influenza gene segments can be derived from different influenza strains, either pandemic or interpandemic ones. This can result in reassorted influenza viruses which combine the genes for the surface glycoproteins hemagglutinin (HA) and/or neuraminidase (NA) of actual interpandemic viruses with five or six or seven RNA segments coding for other proteins from the attenuated master strain, for example a 6/2 combination comprising HA and NA segments from a different strain, or 7/1 reassortants comprising HA or NA segment from a different strain or 5/3 reassortants containing HA, NA and M segments of a circulating strain respectively.

According to a specific embodiment, the influenza virus is lacking functional NS1 and functional PB1-F2 proteins.

The modification or deletion of the NS1 and PB1-F2 reading frame has several positive effects. Deletion of two genes from the genome of vaccine viruses increases genetic stability of their attenuated phenotype and brings safety to a higher level. In case of partially truncated NS1 mutants, which are capable of replicating in the respiratory tract, the PB1-F2 deletion enchances the virus clearance triggered by the innate immune system. Moreover, deletion of the PB1-F2 increases immunogenicity of the vaccine due to better attraction and activation of immune competent cells like macrophages or dendritic cells. Such cells infected by the double deletion mutant virus elicit higher interferon-alpha levels early after infection compared to a virus containing only NS1 deletion. Better induction of cytokines modulates and stimulates the adaptive immune response. Specifically, the deletion of the PB1-F2 reading frame in addition to the NS1 leads to increased levels of IgG, specifically of IgG1 and IgG2A antibody response in mice. Higher antibody response provides better protection of animals against the highly pathogenic influenza challenge virus.

Due to increased immunogenicity the dose of the double deletion mutant to induce an immune response could be lower compared to influenza virus comprising only delNS1 phenotype.

Surprisingly, genetic modification of the virus by deletion of two pathogenicity factors could even enhance viral growth in Vero cells early after infection, improving production efficiency of vaccine strains.

Also a vaccine composition comprising an immunogenically-inducing effective amount of the virus according to the invention in admixture with a pharmaceutically acceptable carrier is covered. Adjuvants and stabilizers can also be contained in the composition.

According to the invention the term "immunogenic" means that the virus is capable of eliciting humoral or cellular immune response, and preferably both. An immunogenic entity is antigenic, too. An immunogenically inducing effective amount of virus elicits humoral or cellular immune response, or both, when administered to an animal, preferably to a human.

The vaccine composition may be used for prophylactic treatment of influenza disease comprising administering to a human patient in need of treatment an immunologically inducing effective amount of the composition.

The compositions may be used in methods or as medicaments in preventing, managing, neutralizing, treating and/or ameliorating influenza virus infection. The use of an influenza virus according to the invention in the manufacture of a medicament for treatment of an influenza virus infection is of course included.

The immunogenic compositions may comprise either a live or inactivated influenza virus of the invention. The virus can be inactivated by methods well known to those of skill in the art. Common methods use formalin and heat for inactivation.

A live immunogenic formulation may be preferred due to increased immunogenicity. Production of such live recombinant immunogenic formulations may be accomplished using conventional methods involving propagation of the virus in cell culture or in embryonated eggs (e.g., embryonated chicken eggs) followed by purification.

The term "pharmaceutically acceptable" means approved by a regulatory agency of the Federal or a state government or listed in the U.S.

The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration. The particular formulation may also depend on whether the virus is live or inactivated.

The term adjuvant refers to a compound or mixture that enhances the immune response to an antigen. The term stabilizers refers to any agent that can increase the stability of the inventive virus, for example it can be bovine serum albumin, sugars, chitosan, dextrans, PEGs etc.

Methods of introduction include but are not limited to intradermal, intramuscular, intraperitoneal, intravenous, intranasal, epidural or oral routes. Introduction by intranasal routes is preferred.

In a preferred embodiment it may be desirable to introduce the medicament into the lungs by any suitable route.

Pulmonary administration can also be employed, using e.g. an inhaler or nebulizer or formulate it with an aerosolizing agent.

The pharmaceutical preparation can also be delivered by a controlled release system, like a pump.

Alternatively, a ready-to-use infusion solution is provided. Alternatively, the preparation can be formulated as powder which is solved in appropriate aqueous solutions immediately before application.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for administration are generally about $10^4$-$5\times10^7$ pfu and can be administered once, or multiple times with intervals as often as needed. Pharmaceutical compositions of the present invention comprising $10^4$-$5\times10^7$ pfu of mutant replication deficient viruses can be administered intranasally, intratracheally, intramuscularly or subcutaneously. Effective doses may be extrapolated from dose-response curves derived from in vitro or animal model test systems.

Of course the invention also provides a method for preventing influenza virus infection of a patient comprising administering the inventive vaccine to an individual.

The invention also provides the use of the inventive virus for preparing a preparation for preventing influenza virus infection of an individual.

The foregoing description will be more fully understood with reference to the following examples. Such examples are, however, merely representative of methods of practicing one or more embodiments of the present invention and should not be read as limiting the scope of invention.

Examples

PB1-F2 Mutagenesis

Mutagenesis of PB1-F2 is done using standard molecular biological methods (e.g. PCR, site directed mutagenesis) or by custom gene synthesis at Geneart AG (Germany). All constructs are sequenced to verify the absence of unwanted mutations.

TABLE 1

| Nucleotide mutations according to SEQID1 | AA substitutions in F2 according to SEQID 3 | AA position according to SEQID3 |
|---|---|---|
| T120C | M to T | 1 |
| T153G | L to Stop | 12 |
| T222A | L to Stop | 35 |
| T234C | M to T | 39 |
| T255C | M to T | 46 |
| T270C | M to T | 51 |
| G291A | W to Stop | 58 |

T120C: M to T
T153G: L to Stop
T222A: L to Stop
T234C: M to T
T255C: M to T
T270C: M to T
G291A: W to Stop All amino acid substitutions in the F2 ORF are silent mutations with respect to the PB1 ORF.

Virus Rescue

Virus rescue of PB1-F2 wild-type and PB1-F2 mutant viruses is done from plasmids using a bidirectional 8-plasmid system developed by Erich Hoffmann (Hoffmann et al. 2000, PNAS 97(11):6108-13).

Briefly, Vero cells (recommended by the WHO for vaccine production) are co-transfected with eight plasmids each containing one of the respective Influenza A segments according to a previously optimised protocol. Following transfection, cells are incubated in serum-free medium containing trypsin to allow viral replication. Usually three to four days later a strong cytopathic effect caused by viral replication is observed. At this time viruses are harvested and either frozen until further usage or directly used for preparation of viral stocks.

Cultivation of Viruses

Cultivation and evaluation of growth characteristics is done in serum free Vero cells culture. Titration of viral stocks is performed by $TCID_{50}$ method on 96 well plates according established SOPs.

Material and Methods

Mice and Immunizations.

Young adult approximately eight weeks old female C57Bl mice were immunized twice i.n. under ether anaesthesia with two reassortant viruses A/Kurgan/5/05delNS1 (6:2 reassortant based on influenza virus IVR-116) with or without PB1-F2 ORF. Dose per mouse was adjusted to 5,5 lg TCID50 in case of A/Kurgan/5/05 6:2 delNS1 and 5,4 lgTCID50 in case of A/Kurgan/5/05 6:2 delNSdelPB1-F2. The interval between immunizations was 28 days.

Generation of Serum Samples

Blood was collected from the murine retroorbital venous plexus at days 28 after first immunization and at day 20 after the second immunization. Blood samples clotted at room temperature for 2 hours and serum was generated following centrifugation (4000 rpm, 10 min), and finally stored at −20° C.

Growth Potential of Virus Variants

To evaluate the potential of reassortant virus to grow in Vero cells, $TCID_{50}$ assays were performed from supernatants collected from infected wells at different time-points. In brief, fresh Vero cell monolayer (6-wells plates) were inoculated with both reassortant viruses: A/Kurgan/5/05 6:2 delNS and A/Kurgan 5/05 6:2 delNSdelPB1-F2 at MOI=0.01; 0.001 and 0.0001 (two wells for each MOI). After 40 min of incubation at room temperature, inoculi were removed and assay medium (OPTIPRO® medium; Invitrogen), supplemented with 4 mM L-Glutamine (GIBCO) and 5 μg/ml trypsin (Sigma)] was added. Cells were incubated at 37° C. and 5% $CO_2$. After 24, 48 and 72 hours aliquots (300 μl) from two wells were combined and frozen at −80° C. Then, all samples were thawed and titrated in Vero cells by the TCID50 assay. Serial 10-fold dilutions of frozen supernatants were prepared in assay medium. 100 μl of the diluted samples were added to wells of a 96-well plate containing fresh Vero cell monolayers. Cells were incubated at room temperature for 50 min. Inoculum was removed and fresh assay medium was added. Cells were incubated at 37° C. and 5% $CO_2$ for 3 days. Infected and non-infected wells were scored microscopically and supernatants were also assessed by the HA assay utilizing 0.5% chicken RBC. The $TCID_{50}$ titre was calculated using the method of Reed and Muench.

ELISA

A modified enzyme-linked immunosorbent assay (ELISA) protocol was performed Briefly, 96-well clear NUNC MAXISORP plates were coated overnight with purified H5N1 reassortant virus A/Kurgan/5/05 (40 HAU/well) at 4.degree. C. Plates were then washed, blocked for 30 minutes with PBS containing 0.5% I-block (TROPIX) and 0.01% TWEEN (assay buffer) and serial dilutions of serum (100 μl/well) were added to coated wells and incubated for 2 hours at room temperature. After extensive washing, bound antibodies were detected with affinity-purified goat anti-human IgG1 (0.5 μg/ml, Invitrogen) or IgG2a (1 μg/ml, Invitrogen) conjugated with horseradish peroxidase (100 μl/well) followed by additional washing steps and subsequent addition of substrate TMB (100 μl/well, KPL). The reaction was stopped with 2 M H.sub.2SO.sub.4 and the optical density (OD) measured (measure wavelength 450 nm; reference wavelength 630 nm). The cut-off value was defined as OD value of 0.15 exceeding the mean absorption value of negative control sera plus two standard deviations.

Isolation of Splenocytes

Spleens of immunized mice (three mice per group) were collected at day 10 (CD8+ T cell ELISPOT) and day 28 following priming (CD4+ T cell ELISPOT). Spleens were mechanically dissociated into single cell suspensions by means of cell strainers (Falcon). The erythrocytes present in the cell suspensions were lysed with Tris-buffered ammonium chloride, several times washed and finally resuspended in Dulbecco's Modified Eagle's Medium (DMEM) containing 10% FCS, penicillin, streptomycin, IL-2 (30 U/ml) and 50 μM 2-mercaptoethanol.

ELISPOT Assays

An immediate ex vivo CD8+ and CD4+ IFN-γ enzyme-linked immunospot (ELISPOT) assay was performed utilizing following synthetic peptides: ASNENMETM (SEQ ID NO:5) an H-$2D^b$-restricted immunodominant CTL epitope of the conserved influenza A virus nucleoprotein (NP147-155; CD8+ ELISPOT) and a pool of IRPNENPAHKSQLVW (SEQ ID NO:6) and INDRNFWRGENGRKT (SEQ ID NO:7) H-$2D^b$-restricted CD4+ peptides (NP 316-330 and 201-215 respectively, CD4+ ELISPOT) from conserved influenza A virus nucleoprotein. Briefly, twofold serial dilutions of cell populations derived from murine spleens were transferred to wells coated with anti-mouse IFN-γ monoclonal antibody (MAb R4-6A2, BioLegend). Cells were incubated for 24 h (CD8+ ELISPOT) or 48 h (CD4+ ELISPOT) at 37° C. and 5% $CO_2$ in DMEM containing 10% fetal calf serum, IL-2 (30 U/ml), penicillin, streptomycin, and 50 μM 2-mercaptoethanol in the presence of peptides. A biotinylated anti IFN-γ MAb (XMG1.2, BioLegend) was utilized as a conjugate antibody, followed by incubation of plates with streptavidin peroxidase (0.25 U/ml; Boehringer Mannheim Biochemica). Unstimulated cells and cells stimulated with TYQRTRALV-an H-$2K^d$-restricted immunodominant CTL peptide (SEQ ID NO:8) served as negative controls. Spots representing IFN-γ-secreting CD8+ cells were developed utilizing the substrate 3-amino-9-ethylcarbazole (Sigma) in the presence of hydrogen peroxide in 0.1 M sodium acetate, pH 5.0. The spots were counted with the help of a dissecting microscope, and the results were expressed as the mean number of IFN-γ-secreting cells/$10^6$ cells±standard error of mean (SEM) of triplicate cultures. Cells incubated in the absence of synthetic peptides developed <15 spots/$10^6$ cells.

Induction of IFN-α in Human PBMCs

Cells:

Peripheral blood mononuclear cells (PBMCs) were obtained by gradient centrifugation with Lymphocyte separation medium (PAA) from venous blood of four volunteers. Cells were washed several times with RPMI 1640 medium (Gibco) and frozen before usage.

TABLE 2

| Virus | Passage history/modifications | TCID50/m | Short title |
|---|---|---|---|
| A/Chicken/Kurgan/5/05 | Transfection on Vero cells: HA, NA from A/Chicken/Kurgan/5/05, all other fragments from IVR-116; NS1 deletion | $5.21*10^7$ | Kurgan 6: 2 ΔNS |
| A/Chicken/Kurgan/5/05 | Transfection on Vero cells: HA, NA from A/Chicken/Kurgan/5/05, all other fragments from IVR-116; PB1 f2 deletion; NS1 deletion | $1.25*10^7$ | Kurgan PB1 f2 ΔNS |

Viruses were cultured on Vero cells (3 passages); these cells were also used for virus-$TCID_{50}$ titers determination.

Cells Infection Procedure:

One day before infection cells were thawed, washed with RPMI 1640 containing 10% FBS (Gibco) and left for 24 h to rest at 37 C 5% $CO_2$ in aliquots ($1*10^6$ cells/tube). After incubation, cells were washed and infected with various Kurgan virus modifications at a multiplicity of infection (moi) of 2 or mock infected (RPMI 1640). After an inoculation time of 30 min, the cells were spun down and resuspended in 1 ml RPMI 1640 medium containing 10% FCS and incubated at 37° C. and 5% $CO_2$. Supernatants were harvested at 6 h and 24 h (p.i.) and the levels of IFN-α were determined by using quantitative cytokine-specific ELISA kit.

Virus Clearance Test in Mice

Mice are infected intranasaly with $10^6$ virus particles per animal of the NS1 mutant virus comprising 125 or 80 amino acid residues in combination (or without) with the deletion of PB1-F2 readin frame. On day 2, 4, 6, 7 and 8 after infection mice lungs are removed and the viral load is assessed by titration of the lung homogenates (TCID50) in Vero cells. The first day of the full viral clearance (lack of the detectable virus) from the lungs is defined Protection in Mice Against Challenge with Highly Pathogenic H5N1 Strain Groups of mice (n=20) were immunized intranasally with equal doses of two reassortant viruses containing surface glycoproteins HA and NA of A/Chicken/Kurgan/5/05 (H5N1) strain and keeping the single NS1 or double deletion NS1/PB1-F2 as attenuation factors. Four weeks later mice were challenged intranasally with the wild type highly pathogenic, homologous A/Chicken/Kurgan/5/05 (H5N1) strain taken in a dose of 50 $LD_{50}$. The lethality after challenge was followed during 15 days and percentage of the dead animals was defined.

Results

DelNS1-PB1-F2 Variant Shows an Enhanced Growth Potential in Vero Cells

Vero cell were infected with delNS1 and delNS1-PB1-F2F2 virus variants as described in Material and Methods section in more detail. Irrespective of the MOI used delNS1-PB1-F2 virus variant replicated to significantly higher TCID50 titers 24 hours post infection when compared with delNS1 virus. The data as shown in FIG. 1 indicate that the deletion of the PB1-F2 protein has a positive effect on virus growth in the production substrate—the Vero cells.

Increased Interferon-α Induction by DelNS1-PB1-F2 Variant

Human PBMCs from different donors were infected with equal doses of delNS1 and delNS1-PB1-delF2 virus variants as described in Material and Methods section. Six hours post infection the level of interferon-2a was measured in the culture supernatants by ELISA kit. Double deletion mutant appeared to elicit higher interferon production in all four cultures of PBMCs compared to NS1 deletion virus (table 3, FIG. 7). Thus, the deletion of PB1-F2 protein abrogates capacity of the virus to inhibit the innate immune response after infection of immune competent cells.

TABLE 3

| IFN-α levels (pg/ml) 6 h p.i. | | | | | | | |
|---|---|---|---|---|---|---|---|
| | IFN-α 6 h p.i. | | | | mean | sd | sem |
| Kurgan 6: 2 ΔNS | 48.41 | 65.43 | 25.02 | 90.8 | 57.41 | 27.74 | 13.87 |
| Kurgan 6: 2 PB1delf2 ΔNS | 69.89 | 108.94 | 64.05 | 134.4 | 94.32 | 33.34 | 16.67 |
| Mock | 10.03 | 11.87 | 10.72 | 10.42 | 10.76 | 0.79 | 0.39 |

Detection of H5 Specific IgG1 and IgG2a in Mouse Sera.

Serum samples collected at day 28 after first immunization and at day 20 after second immunization were analyzed for the presence of virus-specific IgG1 and IgG2a antibodies (FIG. 2) Interestingly, mice immunized with the delNS1-PB-1F2 mutant virus developed markedly enhanced titers of virus-specific IgG1 antibodies following the first immunization whereas mice immunized with the delNS1 parent virus needed a booster immunization to reach virus-specific IgG1 levels comparable to those of mice primed with the delNS1-PB1-F2 variant. As for, virus-specific IgG2a antibody geometric mean titers (Th1 type of immune response) were comparable for both groups of mice immunized after first immunization, however after second immunization advantage of delNS1-PB1-F2 variant was also revealed These data indicate that the deletion of F2 reading frame in the delNS1-PB1-F2 variant stimulates significantly the Th2 type of immune response and thus may contribute to a broader spectrum of virus-specific antibodies and enhanced protection of immunized hosts.

In FIG. 2 the results are shown when mice were immunized twice with delNS1-PB1F2 and delNS virus mutants. Serum samples collected at day 28 after first immunization (single) and at day 20 after second immunization (second) were analyzed for the presence of virus-specific IgG1 and IgG2a antibodies. Shown are end-point titres of individual mice. Horizontal line segments represent the geometric mean titer of the entire group of mice immunized with the respective virus variant as indicated in the figure.

Determination of T-cell Immune Response in Mice

Mice immunized with delNS-PB1F2 virus variant were capable of developing the same magnitudes of virus-specific CD6+ T cells when compared with mice immunized with the delNS virus. Specific CD4+ T cell stimulation of mice with helper epitope peptides resulted in both groups of virus-immunized mice in low frequency of IFN-γ spot forming CD4+ T cells close to the range of the control mice.

TABLE 4

| Determination of T-cell immune responses in immunized mice. | | |
|---|---|---|
| Immunization | IFN-γ spot forming cells/$10^6$ cells (±S.E.M.) | |
| group (Virus) | CD8+ T cells | CD+4 T cells |
| delNS | 51 (11.3) | 31 (3.3) |
| delNSdelPBF2 | 50 (3.3) | 25 |
| control | <10 | 22 |

Spleens of immunized and control mice were obtained at days 10 (CD8+ T cell ELISPOT) and 28 (CD4+ T cell ELISPOT) after immunization from three mice per group and were pooled, dissociated to single cell populations and the ELISPOT assay performed as described in Materials and Methods section. Shown is the mean of IFN-γ secreting cells per million cells plus standard error of mean (S.E.M.)

The Clearance of the Partially Truncated NS1 Mutant Viruses from the Mouse Respiratory Tract.

In contrast to complete NS1 deletion viruses which are replication deficient in vivo, viruses with only partially truncated NS1 proteins, namely comprising amino acids 1-125 or 1-80 amino acid residues are capable of replicating to some extent in the respiratory tract of mice. These viral mutants containing or not containing active PB1-F2 open reading frame are compared for the extent and duration of the virus replication in the different parts of the respiratory tract. Experiment allows demonstrating increased attenuation of the viruses containing deletion of the PB1-f2 protein. The example shows that additional deletion of PB1-F2 pathogenicity factor ensures the safety profile of the attenuated (replication competent) live intranasal vaccine strains.

Deletion of the PB1-F2 Increases Efficacy of the Intranasal Replication Deficient Vaccine Single intranasal immunization of mice with 5 log of two vaccine model viruses containing single NS1 or double NS1/PB1-f2 deletion, based on a A/Chicken/Kurgan/5/05 (H5N1) virus, were capable of inducing protection against lethality induced by the challenge with the highly pathogenic homologous strain in a different extent. The vaccine based on a double deletion virus protected 100% of the animals, whereas only 37 percent of animals were protected after immunization with NS1 deletion mutant virus. In the mock control group immunized with the PBS lethality level has reached 95% during 15 days period of observation. Thus NS1/PB1-F2 double deletion mutant vaccine virus is superior in protection efficacy compared to a vaccine virus containing only single NS1 deletion.

The invention claimed is:

1. An influenza virus, wherein the virus is replication deficient in interferon-competent cells and lacks functional NS1 and PB1-F2 proteins, wherein the NS1 protein of the virus is deleted, wherein the virus comprises a PB1 gene having an open reading frame which is modified by introduction of at least one stop codon by modification of any of positions T120, T153, T222, T234, T255, T270 and G291 according to the numbering of SEQ ID NO:1, and wherein the replication rate of the virus in interferon competent cells is at least less than 5% than that of the wild type influenza virus.

2. The influenza virus of claim 1, wherein the PB1 gene is modified by introduction of multiple stop codons.

3. The influenza virus of claim 1, wherein the PB1 gene of the virus is modified and results in the knock out of the PB1-F2 gene.

4. The influenza virus of claim 1, wherein the virus comprises the nucleotide sequence of SEQ ID NO:2.

5. The influenza virus of claim 1, wherein the PB1-F2 protein comprises the amino acid sequence of SEQ ID NO:4.

6. The influenza virus of claim 1, wherein the NS gene encodes a truncated NS1 protein.

7. A vaccine comprising the influenza virus of claim 1, and a pharmaceutically acceptable carrier.

8. The vaccine according to claim 7, wherein the vaccine is formulated for intranasal delivery.

9. A method of preventing disease caused by influenza virus infection in an individual comprising the step of administering a therapeutically effective amount of the vaccine of claim 7 to the individual.

10. The method of claim 9, wherein the vaccine is administered intranasally.

* * * * *

SEQUENCE LISTING

```
<160> NUMBER OF SEQ ID NOS: 4

<210> SEQ ID NO 1
<211> LENGTH: 2341
<212> TYPE: DNA
```

-continued

<213> ORGANISM: Influenza virus

<400> SEQUENCE: 1

```
agcgaaagca ggcaaaccat ttgaatggat gtcaatccga ctttactttt cttgaaaatt     60
ccagcgcaaa atgccataag caccacattc ccttatactg gagatcctcc atacagccat    120
ggaacaggaa caggatacac catggacaca gttaacagaa cacatcaata ttcagaaaaa    180
gggaaatgga caacaaacac agaaactggg gcgccccaac ttaacccgat tgatggacca    240
ctacctgagg ataatgagcc aagtggatat gcacaaacag actgtgtcct ggaagctatg    300
gctttccttg aggaatccca cccagggatc tttgaaaact cgtgccttga aacaatggaa    360
gtcgttcaac aaacaagagt ggacagactg acccaaggtc gtcagaccta tgattggaca    420
ttaaacagaa atcaaccagc cgcaactgca ttagccaaca ctatagaagt tttcagatcg    480
aatggtctaa cagctaatga gtcgggaagg ctaatagatt tcctcaagga tgtgatggaa    540
tcaatggata aagaggaaat agagataaca acacacttcc aaagaaaaag aagagtaaga    600
gacaacatga ccaagaaaat ggtcacacaa agaacaatag gaaagaaaaa gcagagagtg    660
aacaagagaa gctatctaat aagagcatta actttgaaca caatgaccaa agatgcagaa    720
agaggtaaat taaagagaag agctattgca acacccggga tgcaaatcag agggttcgtg    780
tactttgttg aaactctagc taggagcatt tgtgagaagc ttgaacagtc tggacttcca    840
gtaggaggta atgaaaagaa ggccaaactg gcaaatgttg tgagaaagat gatgactaat    900
tcacaagaca cagagctttc tttcacaatt actggagaca atactaagtg gaatgaaaat    960
caaaatcctc gaatgttcct ggcgatgatt acatatatca caaaaaatca acctgaatgg   1020
ttcagaaaca tcctgagcat cgcacccata atgttctcaa acaaaatggc gagactaggg   1080
aaaggataca tgttcgaaag taagagaatg aagctccgaa cacaaatacc agcagaaatg   1140
ctagcaagca ttgacctaaa gtatttcaat gaatcaacaa gaaagaaaat tgagaaaata   1200
aggcctcttc taatagatgg cacagcgtca ttgagccctg gaatgatgat gggcatgttc   1260
aacatgctaa gtacggtttt aggagtctca atactgaatc ttgggcaaaa gaaatacacc   1320
aaaacaacat actggtggga tgggcttcaa tcctctgatg attttgctct catagtgaat   1380
gcaccaaatc atgagggaat acaagcagga gtggatagat tctacagaac ctgcaagcta   1440
gtcggaatca atatgagcaa gaagaagtcc tatataaata ggacaggaac atttgaattc   1500
acaagctttt tttatcgcta tggatttgtg gccaatttta gcatggagct gcccagtttt   1560
ggagtgtctg ggattaatga atcagctgat atgagcattg gagtaacagt gataaagaac   1620
aacatgataa acaatgacct tggaccagca acagcccaga tggctcttca actgttcatc   1680
aaggactaca gatatacata tcggtgccac agaggagaca cacaaattca gacgaggaga   1740
tcatttgagc taaagaagct gtgggagcaa acccgatcaa aggcaggact attggtttca   1800
gatggaggac cgaacttata caatatccgg aatcttcaca tccctgaagt ctgcttaaag   1860
tgggagctaa tggatgaaga ctatcaggga agactttgta atcccctgaa tccatttgtc   1920
agccataaag agattgagtc tgtaaacaat gctgtggtaa tgccagctca tggtccagcc   1980
aagagcatgg aatatgacgc tgttgcaact acacactcct ggattcccaa gaggaaccgc   2040
tctattctca acacaagcca aaggggaatt cttgaggatg aacagatgta tcagaagtgc   2100
tgcaacctgt tcgagaaatt tttccccagt agttcataca ggagaccggt tggaatttcc   2160
agcatggtgg aggccatggt gtctagggcc cggattgatg ccagaattga cttcgagtct   2220
ggacggatta agaaagaaga gttctccgag atcatgaaga tctgttccac cattgaagag   2280
```

ctcagacggc aaaaacaatg aatttagctt gtccttcatg aaaaaatgcc ttgtttctac 2340
t 2341

<210> SEQ ID NO 2
<211> LENGTH: 2341
<212> TYPE: DNA
<213> ORGANISM: artificial
<220> FEATURE:
<223> OTHER INFORMATION: influenza virus with modified PB1 gene (GHB01 PBdelF2)

<400> SEQUENCE: 2
agcgaaagca ggcaaaccat ttgaatggat gtcaatccga ctttactttt cttgaaaatt 60
ccagcgcaaa atgccataag caccacattc ccttatactg gagatcctcc atacagccac 120
ggaacaggaa caggatacac catggacaca gtgaacagaa cacatcaata ttcagaaaaa 180
gggaaatgga caacaaacac agaaactggg gcgccccaac taaacccgat tgacggacca 240
ctacctgagg ataacgagcc aagtggatac gcacaaacag actgtgtcct agaagctatg 300
gctttccttg aggaatccca cccagggatc tttgaaaact cgtgccttga aacaatggaa 360
gtcgttcaac aaacaagagt ggacagactg acccaaggtc gtcagaccta tgattggaca 420
ttaaacagaa atcaaccagc cgcaactgca ttagccaaca ctatagaagt tttcagatcg 480
aatggtctaa cagctaatga gtcgggaagg ctaatagatt tcctcaagga tgtgatggaa 540
tcaatggata aagaggaaat agagataaca acacacttcc aaagaaaaag aagagtaaga 600
gacaacatga ccaagaaaat ggtcacacaa agaacaatag gaaagaaaaa gcagagagtg 660
aacaagagaa gctatctaat aagagcatta actttgaaca caatgaccaa agatgcagaa 720
agaggtaaat taaagagaag agctattgca acacccggga tgcaaatcag agggttcgtg 780
tactttgttg aaactctagc taggagcatt tgtgagaagc ttgaacagtc tggacttcca 840
gtaggaggta atgaaaagaa ggccaaactg gcaaatgttg tgagaaagat gatgactaat 900
tcacaagaca cagagctttc tttcacaatt actggagaca atactaagtg gaatgaaaat 960
caaaatcctc gaatgttcct ggcgatgatt acatatatca caaaaaatca acctgaatgg 1020
ttcagaaaca tcctgagcat cgcacccata atgttctcaa acaaaatggc gagactaggg 1080
aaaggataca tgttcgaaag taagagaatg aagctccgaa cacaaatacc agcagaaatg 1140
ctagcaagca ttgacctaaa gtatttcaat gaatcaacaa gaaagaaaat tgagaaaata 1200
aggcctcttc taatagatgg cacagcgtca ttgagccctg gaatgatgat gggcatgttc 1260
aacatgctaa gtacggtttt aggagtctca atactgaatc ttgggcaaaa gaaatacacc 1320
aaaacaacat actggtggga tggcttcaa tcctctgatg attttgctct catagtgaat 1380
gcaccaaatc atgagggaat acaagcagga gtggatagat tctacagaac ctgcaagcta 1440
gtcggaatca atatgagcaa gaagaagtcc tatataaata ggacaggaac atttgaattc 1500
acaagctttt tttatcgcta tggatttgtg gccaatttta gcatggagct gcccagtttt 1560
ggagtgtctg ggattaatga atcagctgat atgagcattg gagtaacagt gataaagaac 1620
aacatgataa acaatgacct tggaccagca acagcccaga tggctcttca actgttcatc 1680
aaggactaca gatatacata tcggtgccac agaggagaca cacaaattca gacgaggaga 1740
tcatttgagc taaagaagct gtgggagcaa acccgatcaa aggcaggact attggtttca 1800
gatggaggac cgaacttata caatatccgg aatcttcaca tccctgaagt ctgcttaaag 1860
tgggagctaa tggatgaaga ctatcaggga agactttgta atcccctgaa tccatttgtc 1920

-continued

```
agccataaag agattgagtc tgtaaacaat gctgtggtaa tgccagctca tggtccagcc   1980

aagagcatgg aatatgacgc tgttgcaact acacactcct ggattcccaa gaggaaccgc   2040

tctattctca acacaagcca aaggggaatt cttgaggatg aacagatgta tcagaagtgc   2100

tgcaacctgt tcgagaaatt tttccccagt agttcataca ggagaccggt tggaatttcc   2160

agcatggtgg aggccatggt gtctagggcc cggattgatg ccagaattga cttcgagtct   2220

ggacggatta agaaagaaga gttctccgag atcatgaaga tctgttccac cattgaagag   2280

ctcagacggc aaaaacaatg aatttagctt gtccttcatg aaaaaatgcc ttgtttctac   2340

t                                                                   2341
```

```
<210> SEQ ID NO 3
<211> LENGTH: 90
<212> TYPE: PRT
<213> ORGANISM: Influenza Virus

<400> SEQUENCE: 3

Met Glu Gln Glu Gln Asp Thr Pro Trp Thr Gln Leu Thr Glu His Ile
1               5                   10                  15

Asn Ile Gln Lys Lys Gly Asn Gly Gln Gln Thr Gln Lys Leu Gly Arg
            20                  25                  30

Pro Asn Leu Thr Arg Leu Met Asp His Tyr Leu Arg Ile Met Ser Gln
        35                  40                  45

Val Asp Met His Lys Gln Thr Val Ser Trp Lys Leu Trp Leu Ser Leu
    50                  55                  60

Arg Asn Pro Thr Gln Gly Ser Leu Lys Thr Arg Ala Leu Lys Gln Trp
65                  70                  75                  80

Lys Ser Phe Asn Lys Gln Glu Trp Thr Asp
                85                  90


<210> SEQ ID NO 4
<211> LENGTH: 87
<212> TYPE: PRT
<213> ORGANISM: artificial
<220> FEATURE:
<223> OTHER INFORMATION: mutant PB1F2 protein of influenza virus (GHB01
      delF2)

<400> SEQUENCE: 4

Thr Glu Gln Glu Gln Asp Thr Pro Trp Thr Gln Thr Glu His Ile Asn
1               5                   10                  15

Ile Gln Lys Lys Gly Asn Gly Gln Gln Thr Gln Lys Leu Gly Arg Pro
            20                  25                  30

Asn Thr Arg Leu Thr Asp His Tyr Leu Arg Ile Thr Ser Gln Val Asp
        35                  40                  45

Thr His Lys Gln Thr Val Ser Lys Leu Trp Leu Ser Leu Arg Asn Pro
    50                  55                  60

Thr Gln Gly Ser Leu Lys Thr Arg Ala Leu Lys Gln Trp Lys Ser Phe
65                  70                  75                  80

Asn Lys Gln Glu Trp Thr Asp
                85
```